(12) United States Patent
Rogalska et al.

(10) Patent No.: US 7,393,448 B2
(45) Date of Patent: Jul. 1, 2008

(54) METHOD OF BINDING A COMPOUND TO A SENSOR SURFACE

(75) Inventors: Ewa Maria Rogalska, Nancy (FR); Renata Bilewicz, Warsaw (PL); Denis Etienne Marie André Tagu, Rennes (FR); Alain Georges Ghislain Walcarius, Vandoeurve-les-Nancy (FR); Johannes Wemer, Zuidlaren (NL); Karin Scholtmeijer, Groningen (NL); Rick Rink, Groningen (NL); Harm Jan Hektor, Groningen (NL)

(73) Assignee: Applied NanoSystems B.V., Groningen (NL)

( * ) Notice: Subject to any disclaimer, the term of this patent is extended or adjusted under 35 U.S.C. 154(b) by 1072 days.

(21) Appl. No.: 10/764,270

(22) Filed: Jan. 23, 2004

(65) Prior Publication Data

US 2004/0224137 A1 Nov. 11, 2004

Related U.S. Application Data

(63) Continuation of application No. PCT/NL02/00411, filed on Jun. 21, 2002.

(30) Foreign Application Priority Data

Jun. 21, 2002 (EP) .................................. 01202802

(51) Int. Cl.
*G01N 27/327* (2006.01)
*B05D 3/00* (2006.01)
(52) U.S. Cl. .............................. 205/777.5; 204/403.01; 204/403.09; 204/418; 427/2.11
(58) Field of Classification Search ........................ 204/403.01–403.15; 205/777.5, 778, 792
See application file for complete search history.

(56) References Cited

U.S. PATENT DOCUMENTS

2003/0134042 A1* 7/2003 de Vocht et al. .......... 427/372.2

FOREIGN PATENT DOCUMENTS

WO WO 03/010331 A2 2/2003

OTHER PUBLICATIONS

PCT International Preliminary Examination Report, PCT/NL02/00411, dated Nov. 28, 2003, 7 pages.
PCT International Search Report, PCT/NL02/00411, dated Jul. 21, 2003.
Pum et al., The application of bacterial S-layers in molecular nanotechnology, Jan. 1999, Trends in Biotechnology, pp. 8-12, vol. 17, No. 1.
Bilewicz R. et al., "Modification of electrodes with self-assembled hydrophobin layers", J. Phys. Chem., 105, 9772-9777 (2001).
Nakaminami T. et al., "A biomimetic phospholipid/alkanethiolate bilayer immobilizing uricase and an electron mediator on an Au electrode for amperometric determination of uric acid", Anal. Chem., 71(19), 4278-4283 (1999).

(Continued)

*Primary Examiner*—Alex Noguerola
(74) *Attorney, Agent, or Firm*—TraskBritt (57) ABSTRACT

The present invention relates to a method of non-covalently binding a compound to a sensor surface. The method comprises adsorbing a hydrophobin-like substance to at least a part of the sensor surface, such as an electrode. The invention further provides a sensor having a surface, at least a part of which is provided with a coating of a hydrophobin-like substance that comprises a non-covalently bonded compound.

22 Claims, 5 Drawing Sheets

OTHER PUBLICATIONS

Scholtmeijer K. et al., "Fungal hydrophobins in medical and technical applications", Appl. Microbiol. Biotechnol. 56(1-2), 1-8 (2001).

Tien H.T. et al., "Electrochemistry of supported bilayer lipid membranes: background and techniques for biosensor development", Bioelectrochemistry and Bioenergetics, 42, 77-94 (1997).

Wessels J.G.H. et al., "Hydrophobins: proteins that change the nature of the fungal surface", Adv. Microb. Physiol., 38, 1-45 (1997).

Wosten, H.A.B., et al., "Hydrophobins, the fungal coat unraveled", Biochim. Biophys. Acta, 1469(2):79-86 (2000).

* cited by examiner

METHOD OF BINDING A COMPOUND TO A SENSOR SURFACE

CROSS-REFERENCE TO RELATED APPLICATIONS

This application is a continuation of PCT/NL02/00411, filed Jun. 21, 2002, designating the United States of America, corresponding to PCT International Publication WO 03/010331 (published in English on Feb. 6, 2003), the contents of which are incorporated herein in its entirety.

TECHNICAL FIELD

The present invention relates generally to the field of biotechnology, and more specifically to a method of binding a compound to at least a part of a sensor surface, such as an electrode. The method comprises adsorbing a hydrophobin-like substance to the sensor surface.

BACKGROUND

Hydrophobins are a class of small secreted cysteine-rich proteins of fungi or proteins of bacteria that assemble into amphipathic films when confronted with hydrophilic-hydrophobic interfaces. Some hydrophobins form unstable, amphipathic films and others form extremely stable, amphipathic films. By assembling at a cell wall-air interface, some hydrophobins have been shown to provide for a hydrophobic surface which has the ultrastructural appearance of rodlets as on aerial hyphae and spores. Some hydrophobins have been shown to assemble into amphipathic films at interfaces between water and oils, or hydrophobic solids, and may be involved in adherence phenomena. It appears that hydrophobins are among the most abundantly produced proteins of fungi and individual species may contain several genes producing divergent hydrophobins, possibly tailored for specific purposes.

Hydrophobins have been implicated in various developmental processes, such as formation of aerial hyphae, fruit bodies and conidia, and may play essential roles in fungal ecology including spore dissemination, pathogenesis and symbiosis. Hydrophobins fulfill a broad spectrum of functions in fungal growth and development. For instance, hydrophobins are involved in formation of hydrophobic aerial structures (e.g., aerial hyphae and fruiting bodies) and mediate attachment of hyphae to hydrophobic surfaces resulting in morphogenetic signals. The mechanism underlying these functions is based on the property of hydrophobins to self-assemble at hydrophilic-hydrophobic interfaces into amphipathic films.

Hydrophobins secreted by submerged hyphae diffuse in the aqueous environment and may self-assemble at the interface of the medium and the air. This is accompanied by a drop in water surface tension, enabling hyphae to breach the interface and grow into the air. On the other hand, hydrophobins secreted by hyphae that contact a hydrophobic environment will self-assemble at the hyphal surface. The hydrophilic side of the amphipathic film interacts with the hydrophilic polysaccharides of the cell wall, while the hydrophobic side becomes exposed to the hydrophobic environment. Thus, aerial hyphae and spores become hydrophobic, while hyphae that grow over a hydrophobic substrate firmly attach to the hydrophobic substrate. Hydrophobins are, thus, active in the environment of the fungus and at the hyphal surface. Moreover, the hydrophobins also function within the matrix of the cell wall where the hydrophobins somehow influence cell wall composition. In this case, monomeric hydrophobins, rather than self-assembled hydrophobins, seem to be involved.

The best characterized class I hydrophobin is SC3 of *Schizophyllum commune*, but as far as is known by testing, other members of this class have similar properties. Upon contact with hydrophilic-hydrophobic interfaces, SC3 monomers self-assemble into a 10 nm thick amphipathic film. The hydrophilic and hydrophobic sides of the SC3 membrane have water contact angles of 36° and 110°, making these sides moderately hydrophilic (comparable to carbohydrate) and highly hydrophobic (comparable to TEFLON), respectively.

Interfacial self-assembly of SC3 involves several conformational changes. β-Sheet rich monomers initially adopt a conformation with increased α-helix (α-helix state). SC3 is arrested in this intermediate state at the water-TEFLON interface, but at the water-air interface, the protein proceeds to a form with increased β-Sheet. Initially, this so-called β-Sheet state has no clear ultrastructure (β-Sheet I state), but after a few hours, a mosaic of bundles of 10 nm wide rodlets is observed (β-Sheet II state). This ultrastructural change is not accompanied by a detectable change in secondary structure. The transition from the α-helix state to β-Sheet state can also occur at a water-solid interface, but has to be induced by increasing the temperature and by adding detergent.

Upon self-assembly, the properties of hydrophobins change. Hydrophobins in the β-Sheet state are highly surface active, while monomers have no detectable surface activity. Moreover, lectin activity is increased. In addition, the α-helix state form appears to be less stable than the β-Sheet state. Although both forms strongly adhere to hydrophobic surfaces, the α-helix form can be dissociated and converted to the monomeric formation by treatment with cold, diluted detergents. In contrast, the conformation of the β-sheet form and its interaction with the hydrophobic solid is not affected by this treatment.

Known hydrophobins (see for example WO 96/41882 which also provides guidance to obtain genetically modified hydrophobin-like substances) commonly are proteins with a length of up to 125 amino acids, with a conserved sequence $X_n$-C-$X_{5-9}$-C-C-$X_{11-39}$-C-$X_{8-23}$-C-$X_{5-9}$-C-C-$X_{6-18}$-C-$X_m$ (SEQ ID NO: 5) wherein X, represents any amino acid, and n and m independently represent an integer as disclosed by Wessels et al. (ref. 8).

Most classical hydrophobins contain the eight conserved cysteine residues that form four disulphide bridges. However, when the disulphide bridges of a hydrophobin are reduced by chemical modification and the sulfhydryl groups are blocked with, for example, iodoacetamide, the protein assembles in water in the absence of a hydrophilic-hydrophobic interface. The structure is indistinguishable from that of native hydrophobin assembled at the water-air interface. Apparently, the disulphide bridges of hydrophobins keep monomers soluble in water, e.g., within the cell in which they are produced or in the medium, allowing self-assembly at a hydrophilic-hydrophobic interface but are not necessary to provide for its amphipatic character per se.

Class I and class II hydrophobins are known, each being about 100 amino acids in length and having characteristic hydropathy patterns. Most, but not all, hydrophobins contain eight conserved cysteine residues that form intramolecular disulphide bridges. Hydrophobins may be glycosylated, but the characteristic amphipathic properties of these proteins can be solely attributed to their amino acid sequences. Although the amino acid sequences of class II hydrophobins are relatively well conserved, those of the class I hydrophobins show a low homology. It would be difficult to design universal primers to pick up class I hydrophobin genes by, for example, polymerase chain reaction (PCR).

Indeed, all hydrophobins that have been physically isolated self-assemble at hydrophilic-hydrophobic interfaces into amphipathic membranes. One side of the hydrophobin membrane is moderately to highly hydrophilic (water contact angles below 90°, for example, ranging between 22° and 63°), while the other side exposes a surface with water contact angles essentially above 90°, for example, ranging between 93° and 140°, for example, as hydrophobic as TEFLON (polytetrafluoroethylene) or paraffin (water contact angle at about 110°). The contact angle may be determined by a Drop Shape Angle Analysis System, for example, the DSA10MK2 supplied by Krüss.

The membranes formed by class I hydrophobins (e.g., those of SC3 and SC4 of S. commune) are highly insoluble (resisting 2% sodium dodecyl sulphate (SDS) at 100° C.), but can be dissociated by agents such as formic acid (FA) or trifluoroacetic acid (TFA). In contrast, membranes of the class II hydrophobins cerato-ulmin (CU) of *Ophiostoma ulmi* and cryparin (CRP) of *Cryphonectria parasitica* readily dissociate in 60% ethanol and in 2% SDS, while assembled CU is also known to dissociate by applying pressure or by cooling.

Self-assembly of hydrophobins is accompanied by conformational changes. Monomeric class I and class II hydrophobins are rich in β-sheet structure. At the water-air interface, class II hydrophobins attain more β-sheet structure (called the β-sheet state), while at the interface between water and a hydrophobic solid, a form with increased α-helix is observed (the α-helical state). The α-helical state seems to be an intermediate of self-assembly, whereas the β-sheet state is likely the stable end-form. At the water-air interface, monomers of class I hydrophobins attain the α-helical state within seconds, but the conversion to the β-sheet state is much slower and takes minutes or even hours. At the water-solid interface, the protein also readily attains the α-helical state, but is thought to be arrested in this intermediate state. The β-sheet end state can be reached by applying a combination of heat and diluted detergent. Both forms of the assembled hydrophobin have an amphipathic nature and can be dissociated with TFA, which unfolds the protein.

After removing the solvent and dissolving in water, class I hydrophobins refold to the same monomeric structure that was observed before purification or TFA treatment. However, self-assembly and disassembly of class II hydrophobins can also be repeated even after dissociation of the membrane by TFA. This shows that both classes of hydrophobins are highly resilient to this type of treatment. The membrane of class I hydrophobins is characterized by a mosaic of bundles of 5-12 nm-wide parallel rodlets. In contrast, rodlets have not been found at surfaces of the assembled class II hydrophobins CFTH1 of *Claviceps fusiformis*, CRP of *C. parasitica*, and HFB1 and HFB2 of *Trichoderma reesei*. Whether the absence of rodlets or the differences in rodlet diameter has any functional significance is not yet known.

The rodlets of the class I hydrophobins, SC3 and SC4, of *Schizophylum commune* are very similar to the fibrils formed by amyloid proteins. The rodlets of the class I hydrophobins consist of two tracks of 2-3 protofilaments with a diameter of about 2.5 nm each, have a high degree of β-sheet structure, and interact with the fluorescent dyes Thioflavine T (ThT) and Congo Red. Both dyes may be used as probes to discriminate between the α-helical state and the β-sheet state, each having a high propensity for β-sheet state, but no or lower propensity for α-helix state or soluble hydrophobin-like substance.

In addition, SC3 and amyloid proteins self-assemble via intermediates and only above a critical concentration. It was suggested that amyloid fibril formation is common to many, if not all, polypeptide chains. However, because formation of amyloid fibrils is accompanied by loss of function or even disease (e.g. Alzheimer's disease), evolution would have selected against the propensity to form such fibrils. Yet, one or two mutations in a protein suffice to considerably increase the tendency to form amyloid fibrils. To our knowledge, hydrophobins are the first example of functional amyloids with multiple functions in fungal development. Recently, it was found that the four disulfide bridges of the SC3 hydrophobin are essential to prevent the protein from forming the amyloid structures in the absence of a hydrophilic-hydrophobic interface. When the disulphide bridges were reduced and the sulfhydryl groups blocked with iodoacetamide, the protein spontaneously assembled in water. The protein's structure was indistinguishable from that of native SC3 assembled at the water-air interface. Apparently, the disulphide bridges of hydrophobins keep monomers soluble in water (e.g., within the cell or in the medium) and, thus, prevent precocious self-assembly. This would explain why most hydrophobins have eight conserved cysteine residues in nature.

Hydrophobins belong to the most surface-active molecules. With a maximal lowering of the water surface tension from 72 to 24 mJ m$^{-2}$ at 50 μg ml$^{-1}$, SC3 is the most surface-active protein known. Other hydrophobins are also highly surface active. Their surface-lowering activities are at least similar to those of traditional biosurfactants. In contrast to these surfactants, surface activity is not dependent on a lipid conjugate, but is solely caused by the amino acid sequence. Moreover, while the maximal lowering of the surface tension by the traditional surfactants is attained within seconds, it takes minutes or even hours in the case of class I hydrophobins. This is explained by the fact that hydrophobins lower the water surface after self-assembly that is accompanied by conformational changes in the molecule.

Despite the fact that hydrophobins have diverged considerably, their gross properties are similar. This flexibility is also illustrated by the fact that removing 25 out of 31 amino acids preceding the first cysteine residue of the SC3 hydrophobin to generate truncated SC3 by genetic engineering only affected the wettability of the hydrophilic side of the assembled hydrophobin. A most remarkable hydrophobin is the trihydrophobin CFTH1 of *C. fusiformis*. It contains three class II hydrophobin-like units, each preceded by a Gly-Asn-rich repeat and still behaves like other class II hydrophobins. Because of the interfacial self-assembly into amphipathic protein films, hydrophobins can change the wettability of surfaces.

One method to measure wettability is by estimating or measuring the contact angle that a water drop makes with the surface. A large contact angle (>90°) indicates a hydrophobic surface; a small contact angle (<90°) indicates a hydrophilic surface. Furthermore, in gas/liquid or liquid/liquid systems, such as in vigorously shaken water or in oil-in-water or water-in-oil dispersions, air bubbles or oil droplets in solution of hydrophobin become coated with an amphipathic film that stabilizes them.

Solid/liquid interfaces show the same stabilization. For example, a sheet of hydrophobic plastic, such as TEFLON (contact angle 110°), immersed in hydrophobin becomes coated with a strongly adhering protein film that makes the surface completely wettable (contact angle 48°), even after SDS extraction (contact angle 62°), and hydrophobin monomers dried down on a hydrophilic surface make the surface hydrophobic.

The classical hydrophobins are typically isolated from fungi like *Schizophyllum commune* (ref. 8), but can also be made recombinantly; or comprise a polypeptide having at least 40% identity and at least 5% similarity to at least one polypeptide selected from the group consisting of amino acids 29-131 of SEQ ID NO: 1 and amino acids 29-133 of SEQ ID NO: 2. Such a protein may originate from a filamentous bacterium, in particular, a bacterium capable of forming aerial hyphae, such as an *Actinomycete*, and, more specifically, the filamentous bacterium may be a *Streptomyces* species. A *Streptomyces* species, from which the protein may be isolated using standard procedures for the isolation of hydrophobins, is a *Streptomyces* species which has been transformed with a construct that can be isolated from an *E. coli* strain deposited on 14 Mar., 2000 under accession number CBS 102638 with the Centraalbureau voor Schimmelcultures (Oosterstraat 1, P.O. Box 273, 3740 AG Baarn, the Netherlands). This is disclosed in PCT/NL01/00268.

In particular, Wessels et al. (Advances in Microbial Physiology, 38, pp. 1-45 (1997)) suggest attaching small ligands to a layer of hydrophobin via covalent binding or coupling of amino groups to aldehyde groups on mannose residues (Id. at p. 35). The only example given relates to coupling a protein molecule onto a layer of hydrophobin present on a gold surface. However, coating the surface with a hydrophobin may reduce the sensitivity of the sensor as less surface area is available or reactions to be detected take place at a greater distance from the sensor surface.

SUMMARY OF THE INVENTION

Hydrophobins, whether or not chemically or genetically modified, may be used to change the biophysical properties of a surface. In this way, the binding of molecules or cells to surfaces may be controlled. For instance, the binding of pathogenic bacteria to catheter surfaces could be reduced, while the binding of human fibroblasts to implant surfaces may be encouraged. Apart from changing the biophysical properties, hydrophobins may be used to attach molecules to surfaces that they do not normally have a high affinity with. Attachment may be achieved by chemical cross-linking after the hydrophobin has been assembled on the surface. For example, proteins may be attached to the mannose residues at the hydrophilic side of assembled SC3 via a Schiff-base reaction. Alternatively, in the case of proteins or peptides, fusion proteins may be made and assembled on the surface of interest.

The term "hydrophobin-like substance" as used herein refers to an essentially isolated or purified amphipathic protein capable of coating a surface, rendering a hydrophobic surface essentially hydrophilic or, vice versa, a hydrophilic surface essentially hydrophobic, and comprises not only hydrophobins as isolated from nature and substantially free of other fungal substances, such as carbohydrate polymers like schyzophylan, but also includes substances that can be obtained by chemically modifying known hydrophobins or by genetically modifying hydrophobin genes to obtain genetically modified proteins not at present available from nature, yet still having the desired amphipathic characteristics.

The invention discloses a method of providing a sensor surface with a compound. The method comprises coating at least a part of the surface of the sensor with a hydrophobin-like substance and contacting the compound with the coated hydrophobin-like substance to form a coating. The coating comprises the compound in a non-covalently bound form, or at least not covalently bound to a hydrophobin. In one embodiment, the compound used in the method is an electroactive compound or a compound capable of being converted into an electroactive compound. The method comprises coating an electrode with a hydrophobin-like substance, and contacting the hydrophobin-like substance with the compound to form a coating including the compound in a non-covalently bound form.

A particular type of sensor is an electrochemical sensor comprising an electrode as the sensor surface. Coating an electrode with a hydrophobin would, in general, result in reduced access of electroactive compounds to the surface of the electrode. Surprisingly, it was found that it is possible to non-covalently incorporate a compound in the hydrophobin coating. The compound remains in the hydrophobin coating for a substantial time. Such a compound becomes incorporated when it has a lower molecular weight than the hydrophobin, preferably less than about 2000 daltons and, more preferably, less than about 1000 daltons. The electroactive nature of the compound improves the sensitivity of the electrode as compared to a hydrophobin coating not including the compound.

Another embodiment of the invention relates to a method of providing a sensor of a type having favorable features for use as a biosensor. The biosensor is a device that incorporates a biological recognition element in close proximity, or integrated, with a signal transducer to give an essentially reagent-less sensing system specific to a target compound. In the method, the biological recognition elements are non-covalently attached to a biosensor surface in a non-covalent manner via a hydrophobin-like coating. This mode of binding leaves the secondary and tertiary structure of such biological compounds virtually intact and, thus, allows improved biological recognition as compared to covalent binding methods which often alter such structural determinants.

In another embodiment, a method is provided wherein a first, non-covalently attached compound is a proteinaceous substance with a higher molecular weight than a classically known hydrophobin (i.e., >about 15 kD) but, notwithstanding, becomes non-covalently attached to the coating without essentially losing its reactivity. Surprisingly, substantial non-covalent attachment of such a larger compound to a sensor surface whereby reactivity of the compound, such as enzymatic activity or its propensity to bind to a ligand or antigen, is maintained. The substantial non-covalent attachment of the larger compound to the sensor surface may be achieved by immersing the sensor surface in a solution comprising the compound.

Although covalent linking is thought to be related to the presence of glycosylated hydrophobin, it is disclosed that the surfaces may also be provided with larger molecules having a coating that is essentially devoid of mannose residues that would allow for such covalent linking. This facilitates the use of other hydrophobin-like substances for coating sensor surfaces to which larger molecules may be attached. In an embodiment using S03, which in its natural state is provided with an N-terminal side comprising glycosylated residues, it is also possible to use non-glycosylated substances, such as trSC3 (truncated-SC3) from which the glycosylated N-terminal is absent. In other embodiments, it is possible to use other hydrophobin-like substances characterized by an amphipathic protein character, for example, those not having all the classically conserved cysteine-residues in place and essentially capable of providing a hydrophobic surface with a hydrophilic face, or vice versa.

It is, in particular, herein provided to provide sensor surfaces with molecules of proteinaceous nature. Such molecules may comprise a poly-clonal, mono-clonal, or synthetic antibody, or another binding molecule (which may be additionally provided with an enzyme, such as a peroxidase). The molecules may further comprise an enzyme, such as glucose oxidase, cholesterol oxidase, alkaline phosphatase, luciferase, esterase, lipase, trypsin, other enzymes, or any combinations thereof. The molecules may also comprise a receptor for measuring ligand interaction, such as a light receptor, a light harvesting complex, or combinations thereof. Where covalent binding may result in loss of reactivity, the compounds bound with a method according to the invention substantially maintain their reactivity towards ligands, antigens, substrates, etc., because the bond with the coating is of a non-covalent nature.

Herein, the term "identity" is used in association with a proteinaceous substance such as a polypeptide and is defined, in accordance with the state of the art, as having matched amino acid residues. The sequences may comprise insertions or deletions. The term "similarity" is used in association with proteinaceous substances such as a polypeptide, and denotes conservative substitutions. Conservative substitutions are substitutions in which one amino acid is replaced with another, wherein the following groups of amino acids are considered similar: A, S, T; D, E; N, Q; R, K; I, L, M, V; and F, Y, W.

The term "electroactive" is defined as a compound which can undergo changes in the oxidation state, i.e., undergo a redox reaction. An electroactive compound, such as Q10, azobenzene, Q0 or calixerene will have a lower molecular weight (MW) than the hydrophobin and, in particular, the electroactive compound will have a MW of less than about 2000 daltons and, more preferably, less than about 1000 daltons. Compounds capable of being converted into an electroactive compound are known. The compounds may be electroactive after, for example, irradiation with light. This allows the electroactive compound to be made available at a desired time. Some of the advantages of using such a compound are more accurate measurements (background measurements can be made before the electroactive compound is released) and reduced consumption of electroactive compound. Generally, the compound capable of being converted into an electroactive compound (e.g., calixarene) will have a molecular weight as specified above.

In one embodiment, the electroactive compound is a hydrophobic compound or a compound containing a hydrophobic anchor. Such compounds are most stably maintained in the hydrophobin coating. It is thought that a planar hydrophobic compound or anchor may be beneficial. As used herein, the term "anchor" is understood to mean a part of the compound, such as the part having a side and/or moiety lacking hydrophilic groups. It is also thought that the absence, or a reduced number of negative and/or positive charges is advantageous. If a charge is present, it is preferably from weakly acidic or basic groups which can release or accept a hydrogen ion to eliminate the charge.

In another embodiment, a second compound may be covalently bound to the hydrophobin. The second compound may be an electroactive compound. In another alternative embodiment, the second compound is non-covalently bound to the hydrophobin through a third compound, such as an intermediate compound having affinity for the second compound when the second compound comprises an electroactive compound.

These methods allow for a more selective measurement. With the "first" compound present, good sensitivity is achieved even though the "second" compound is a distance from the electrode surface. Thus, in one embodiment, the second compound is a proteinaceous substance such as redox enzyme or a light receptor. The light receptor may be, for example, a heme-group or a chlorophyl-group.

The invention also relates to an electrode coated with a hydrophobin-like substance, wherein the coating may incorporate a compound that may be an electroactive compound or provided with molecules >about 15 kD. In one embodiment, a sensor includes a sensor surface, at least a part of which is provided with a coating of a hydrophobin-like substance and comprising a non-covalently bound compound.

In another embodiment, a sensor according to the invention is provided wherein the compound is smaller than about 15000 daltons, preferably smaller than about 2000 daltons, or even smaller than about 1000 daltons, as is the case with the electroactive compounds Q10, azobenzene, Q0, calixarene, and others.

In yet another embodiment, a sensor according to the invention is provided wherein the compound is larger than about 15000 daltons, preferably even larger, such as >about 25 kD, considering the average size of, at least, the functional parts of enzymes, receptors, antibodies, and the like. It is herein also provided to non-covalently coat the sensor with a large or small proteinaceous substance, such as a peptide or polypeptide. To perform voltometric analyses, it is preferred that such an analytical system comprises an electrode, such as a glassy-carbon electrode, a gold electrode or a Thin Mercury Film Electrode. The analytical system may further be provided with an electroactive first, second or third compound to improve determining a voltage difference in a solution. The determination comprises contacting the solution with a sensor according to the invention and recording a current.

The electrode may be manufactured using any embodiment of the methods disclosed herein. The electrode may be, for example, a gold or platinum electrode and, in another embodiment, the electrode may be a glassy-carbon electrode (GCE), a glass electrode (GE) or a Thin Mercury Film Electrode (TMFE).

The invention also relates to a method of performing a measurement with an electrode coated with a hydrophobin-like substance. In the method, an electrode produced according to the invention is used. The invention also relates to a sensor comprising an electrode produced according to the invention. Such a sensor may further comprise a means for conducting a measurement, such as lead wires, integrated or non-integrated devices such as an amplifier, a reference electrode, or a signal processing means as is known.

Furthermore, the invention relates to a method of providing a sensor of the type that possesses features favorable for use as a biosensor. Biosensors use biological molecules to detect other biological molecules or chemical substances. Biosensors may, for example, use a monoclonal antibody to detect an antigen or a small synthetic DNA molecule to detect DNA. In a biosensor, a biological recognition (sensing) element is in direct spatial contact with a transducer element to give a reagentless sensing system specific for a target compound (analyte). Transducers are the physical components of the sensor that respond to the products of the biosensing process and may be optical, electrochemical, thermometric, piezoelectric or magnetic. The transducers produce a signal, or a response, from the biosensing, wherein the signal may be in a form that can be amplified, stored, or displayed.

The biological recognition element of the biosensor may be a biological material or a biomimic (e.g., tissue, microorganisms, organelles, cell receptors, enzymes, antibodies, nucleic acids, etc.). Biological sensing elements have a remarkable ability to distinguish between the analyte of interest and similar substances with great accuracy. Biosensing occurs when the analyte is specifically recognized by the biological element. It is preferred that the biological elements are bound to the sensor surface in a non-covalent manner, as is the case in the method provided in the present invention, leaving secondary and tertiary structures of such biological compounds virtually intact and, thus, allowing optimal biological recognition.

For a given analyte-recognition element reaction, several transduction schemes may be applicable. In one transduction scheme, an amperometric device that detects changes in current as constant potential may be used. In another scheme, a conductimetric device that detects changes in conductivity between two electrodes may also be used. In a further scheme, a potentiometric device that detects changes in potential at constant current (usually zero) is used.

In other embodiments, optical transducers may be used. Optical transducers can be subdivided into two modes (extrinsic and intrinsic) according to the optical configuration. In the intrinsic mode, the incident wave is not directed through the bulk sample, but propagates along a wave guide and interacts with the sample at the surface within the evanescent field. Other surface methods of optical detection of biological recognition are based on modulation of the field excited at the interface between different materials due to incident light. For example, the BIAcore system monitors bio-specific interactions with a surface plasmon resonance detector to detect minor mass changes at the surface, such as antibody binding to a surface-immobilized antigen.

A biosensor is distinguished from a bioanalytical system which requires additional processing steps, such as reagent addition. The reagentless form may be achieved by immobilizing the biological recognition element onto the sensor surface. Advantageously, the biosensor surface is coated with a compound allowing non-covalent attachment of a biological recognition molecule. Where covalent binding results in loss of reactivity, the compounds bound using a method according to the invention substantially maintain their reactivity towards ligands, antigens, substrates, etc., probably because the bond with the coating is of a non-covalent nature. In one embodiment, a hydrophobic, gold sensor surface is coated with a hydrophobin solution by simply incubating for some period of time. The surface is washed with water to remove any unbound hydrophobin. Following treatment of the surface with detergent to obtain a β-sheet state coating, the coated surface is used to bind a biological recognition molecule such as antibodies, enzymes, peptides, lipids, nucleic acids or carbohydrates.

The immobilization matrix may function as a support, and it is preferred that the immobilization matrix does not interfere with the sensitivity of the biosensor. Since the mere coating of a sensor surface with hydrophobin would result in reduced signal transmission, it was found that it is possible to incorporate a compound in the hydrophobin coating to increase the sensor performance. In one embodiment, such a compound is an electroactive compound that is incorporated in the hydrophobin coating to improve the sensitivity of the sensor as compared to a hydrophobin coating not including the compound. In a preferred embodiment, the invention discloses a method of providing a sensor surface with a hydrophobin-like substance, wherein the coating further comprises a reactive compound to improve the sensitivity of the sensor, which is also referred to as signal transducer, as well as with a non-covalently bound biological recognition compound.

DETAILED DESCRIPTION

Production and purification of the hydrophobin. HYDPt-1 hydrophobin was produced in *Escherichia coli* as a recombinant polypeptide of 13.7 kDa (ref. 1). Briefly, the hydPt-1 cDNA was cloned in the pQE30 plasmid (Qiagen, Germany) to produce a fusion protein with a His-tag motif. Extraction was performed as described (ref. 1). After chromatographic purification on a $Ni^{2+}$ affinity column, the HYDPt-1 polypeptide was concentrated in 10 mM Tris-HCl by ultrafiltration.

Chemicals and Solutions. All chemicals were of analytical grade. Tris(hydroxymethyl)aminomethane (Tris), dimethyloformamide (DMF) and LiOH were obtained from Fluka. Coenzymes Q0 (2,3-dimethoxy-5-methyl-1,4-benzoquinone) and Q10 (ubiquinone 50) were obtained from Sigma. Diazobenzene was obtained from Reachim, Hungary. Methanol, citric acid and $K_3[Fe(CN)_6]$ were obtained from POCh, Poland. All solutions were prepared daily. Distilled water was passed through a Milli-Q water purification system. The surface tension was 72.5 mN $m^{-1}$ at 20° C. and final resistivity was 18.3 MΩ $cm^{-1}$.

Electrochemical experiments. Voltammetry experiments were done at 20° C. in three-electrode arrangement, with a calomel reference electrode, platinum foil counter electrode and GE, GCE or TMFE as working electrodes. Eco Chemie AUTO-LAB PGSTAT 30 system was used as the potentiostat with an IBM PC and Eco Chemie software. In order to prepare the TMFE, a silver wire or silver disk electrode precleaned in concentrated perchloric acid was touched to a drop of mercury and cathodically polarized in 0.1 M KOH to obtain a shining and uniform layer of mercury, ca. 1 mm thick. The GE and GCE were polished on Buehler polishing papers and paste, and the GE was cleaned in concentrated nitric acid. The electrodes were coated with the self-assembled hydrophobin upon contact with the surface of solutions containing 2 μg of hydrophobin per 1 ml of 10 mM Tris-HCl buffer. The time of the hydrophobin self-assembly and the conditions of Q0, Q10 and diazobenzene adsorption on hydrophobin-coated electrodes are given below.

Barrier properties of HYD Pt-1 films on gold and glassy carbon electrodes. The properties of HYDPt-1 layers adsorbed on hydrophilic and hydrophobic solid surfaces were compared using three different electrode substrates, namely GE, GCE and TMFE. The hydrophilic GE surface was modified with HYDPt-1 by self-assembling the protein at the liquid-air interface and adsorption of the layer to the gold surface. The protein was assembled from 10 mM Tris-HCl buffer, pH 7.0, containing 2 μg/ml hydrophobin, and adsorption to the surface was achieved by lifting up the electrode through the interface or by a horizontal touching of the hydrophobin-covered water surface with the electrode.

Figure 1A:
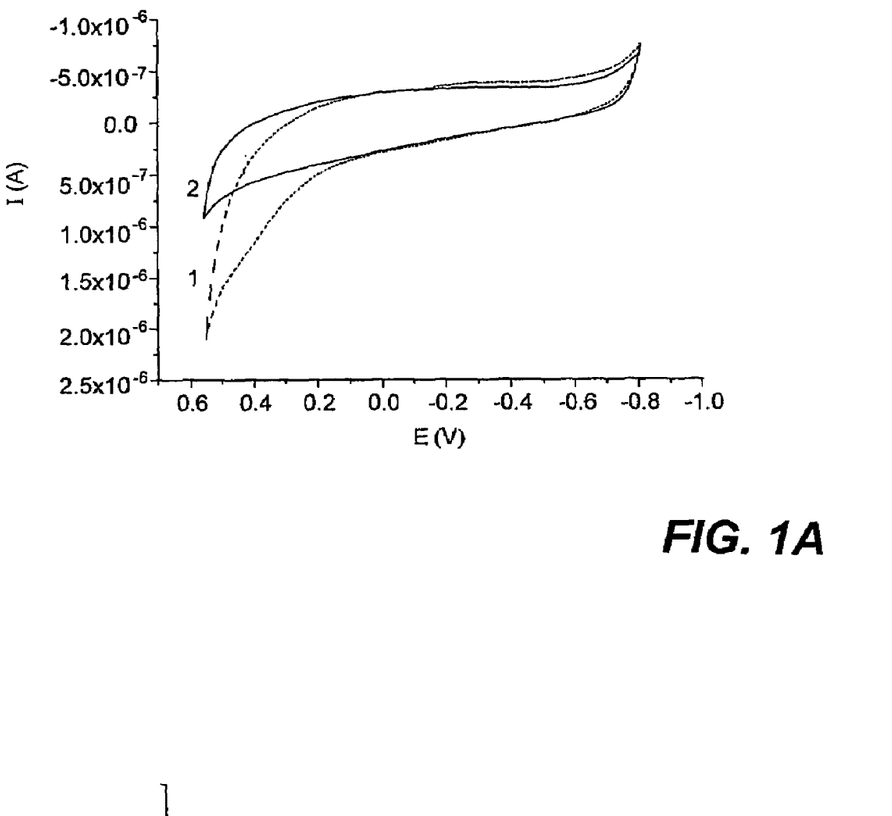
FIGS. 1A-1C show cyclic voltammograms showing the difference between bare (1) and hydrophobin-modified (2) electrodes (GE, GCE, TMFE, respectively).
Figure 1B:
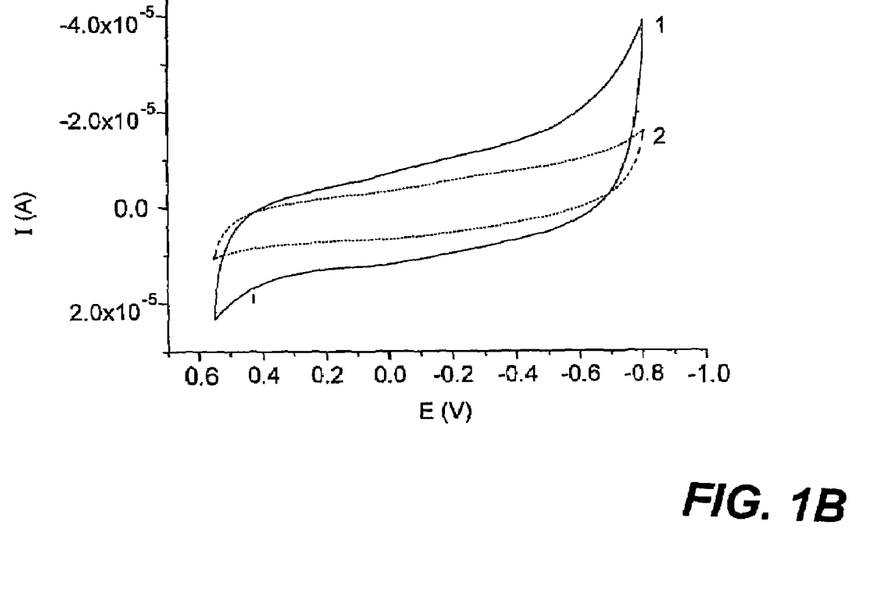
Figure 1C:
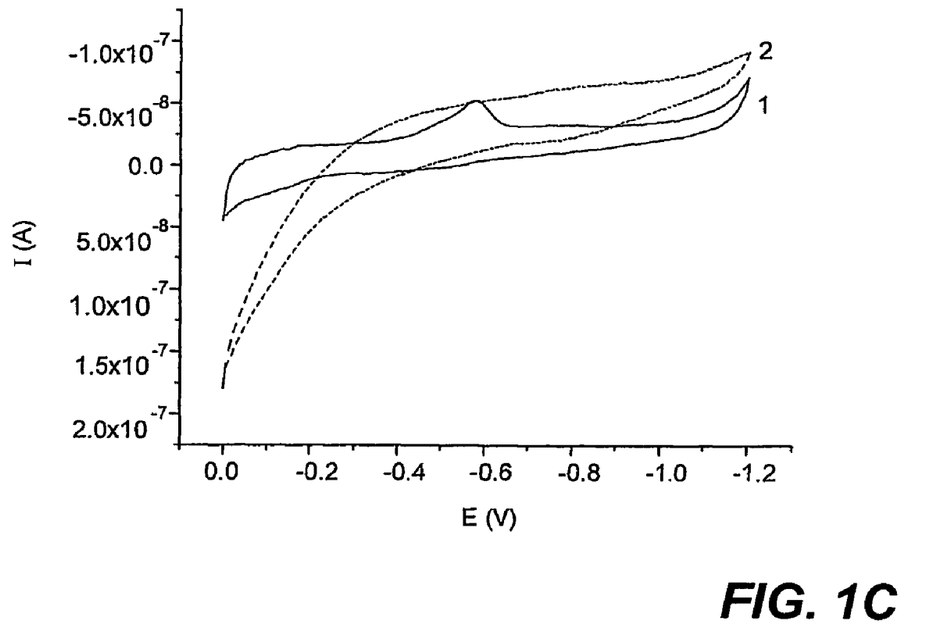

FIG. 1 shows the cyclic voltammograms recorded using the bare (1) and hydrophobin-modified (2) electrodes. FIG. 1A allows the comparison of the bare (1) and covered (2) GE. The curves are similar in that no decrease of background current is observed and no peaks appear in the voltammogram. The presence of the hydrophobin layer on the electrode surface is evidenced by the inhibition of the final increase of anodic current due to gold oxidation. HYDPt-1 is inert in a wide range of potentials and does not lead to a decrease of capacity currents which means that the protein layers formed on the electrode are not as dense and highly blocking as the layers of, e.g., alkanethiols (ref. 2). The extent of blocking is not changed even after 24 hours of self-assembly.

Wessels and Wösten observed that the SC3 hydrophobin had much higher affinity to hydrophobic than to hydrophilic surfaces (ref. 3, 4). Two types of electrodes, GCE and TMFE, were, therefore, chosen as model hydrophobic surfaces to check the behavior of HYDPt-1. The results of self-assembly are shown in FIGS. 1B and 1C, respectively. In both cases, the background currents became much smaller after modification (2), demonstrating that the coverage of GCE and TMFE with HYDPt-1 is much higher, as compared to that of the gold substrate. The protein layers are stable and firmly attached to the electrode substrate as indicated by the GCE voltammogram which does not change over several weeks. In the case of TMFE, high-quality films are formed even when the time of self-assembly is decreased from 24 hours to 20 minutes (FIG. 1C). The capacity of the modified TMFE is significantly lowered and the onset of the mercury oxidation current is shifted towards more positive potentials, revealing strong blocking properties of the hydrophobin layer. An additional peak appears in the TMFE voltammogram at −0.58V. This peak corresponds to the reduction of mercury cysteinate formed on the electrode surface upon oxidation of mercury in the presence of cysteine thiol groups present in the protein.

Stability of HYDPt-1 layers in solutions of different pH. The dependence of stability and blocking properties of HYDPt-1 layers on the pH of the solution was checked by recording multiple cyclic voltammograms using all electrodes in solutions of pH 2.2 (citric acid), pH 4.7 (citric acid/LiOH), pH 7.0, pH 10.2 (Tris), and pH 12.1 (LiOH). The HYDPt-1 layer remained well attached to the electrode surfaces in all solutions studied and the blocking effect on various substrates followed the behavior observed at pH 7.0.

Figure 2A:
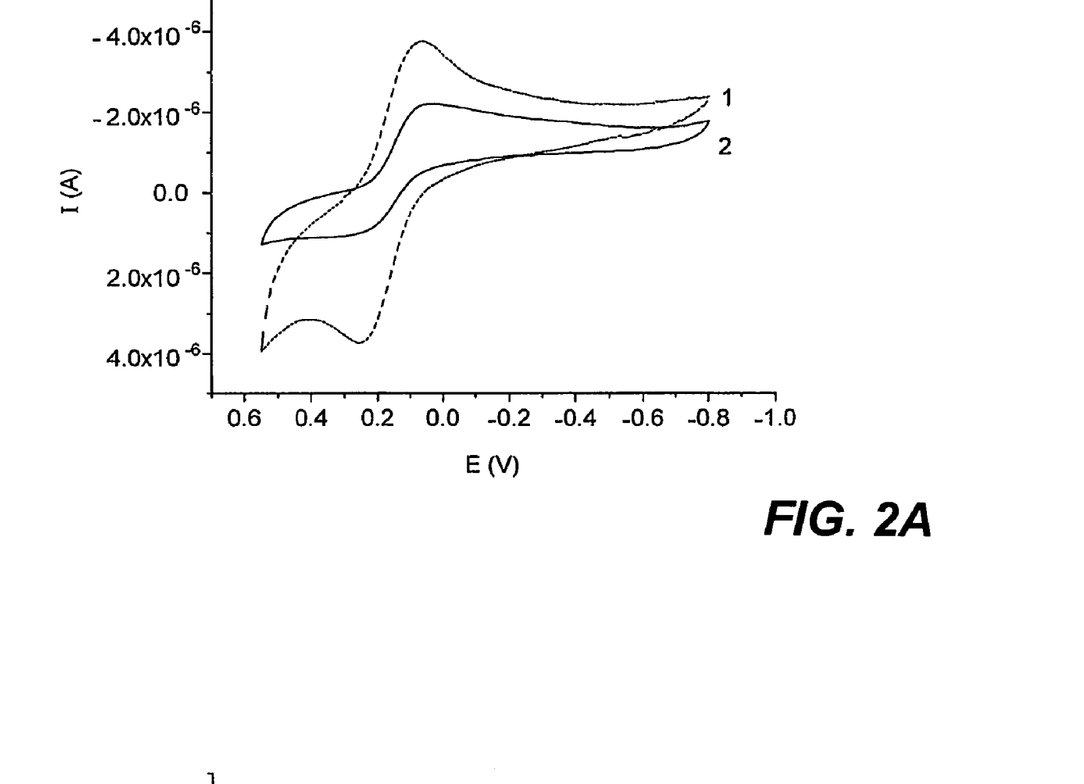
FIGS. 2A and 2B show cyclic voltammograms using ferrocyanate ions as a probe to check the blocking properties of hydrophobin.
Figure 2B:
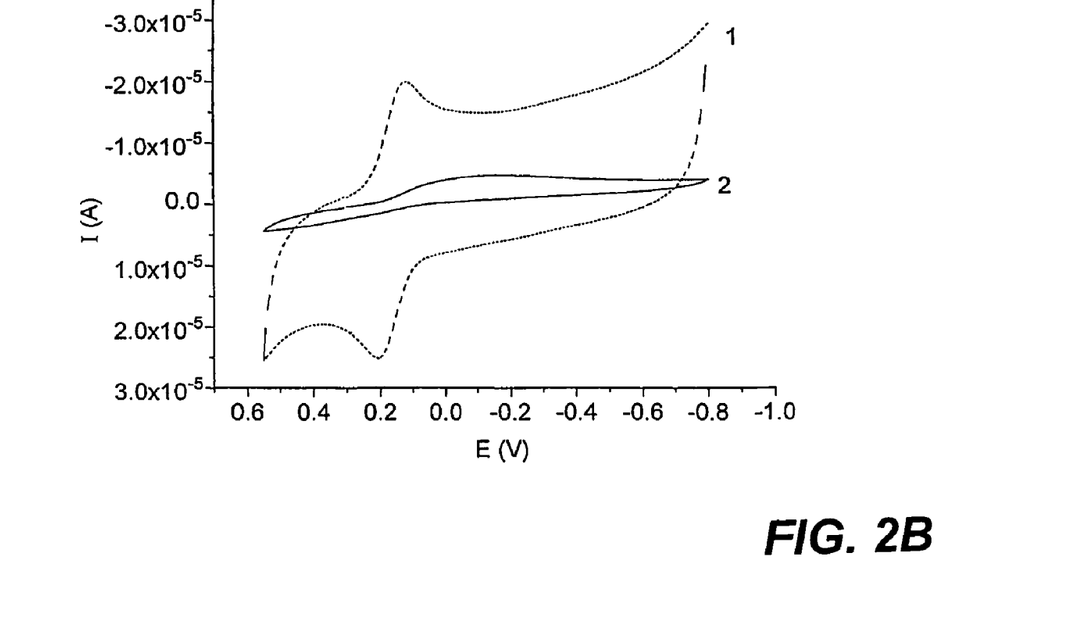

Probing blocking properties of HYDPt-1 layers using ferrocyanate as the electrochemical probe. The ability of small hydrophilic anions to access the electrode surface through the HYDPt-1 layer was checked using ferrocyanate ions as the electrochemical probe. Cyclic voltammograms were recorded in 0.1 M/HClO$_4$ solution containing 0.75 mM K$_3$Fe(CN)$_6$ (FIG. 2). The voltammograms recorded for K$_3$Fe(CN)$_6$ using HYDPt-1-coated (2) electrodes are different as compared to those obtained with a bare (1) GE (FIG. 2a) or GCE (FIG. 2b). The currents are much lower and the voltammetric curves are more sigmoidal in shape. This behavior establishes that the extent of coverage of both electrodes by HYDPt-1 is high and that the probe has a limited access to the electrode surface. The transition from peaked to sigmoidal shape is expected when the access sites are dispersed (ref. 5, 6) and when spherical diffusion becomes the major process for transporting the molecules to the electrode surface, as distinct from the linear diffusion observed for large bare electrodes.

The GCE surface is blocked more efficiently than the gold surface, as shown with the experiments performed in pure supporting electrolyte solution. The latter results confirm a higher affinity of HYDPt-1 towards hydrophobic surfaces.

Hydrophobin as a "molecular glue" for immobilizing molecules on the electrode surface. In the present work, we checked the ability of HYDPt-1 to bind through adsorption to different types of electroactive molecules to electrode surfaces. The long hydrocarbon chain ubiquinone (Q10) was used as a model hydrophobic molecule. The HYDPt-1 layer was self-assembled on the GCE from the usual solution (2 μg/1 ml Tris buffer, pH 7.0). Next, self-assembly of Q10 was carried out from a solution containing 1 mg of Q10 in 1 ml DMF.

Electroreduction of ubiquinone Q10 immobilized on electrodes modified with HYDPt-1. In neutral aqueous solution, ubiquinone undergoes a reduction, according to the following scheme:

Scheme 1

Figure 3A:
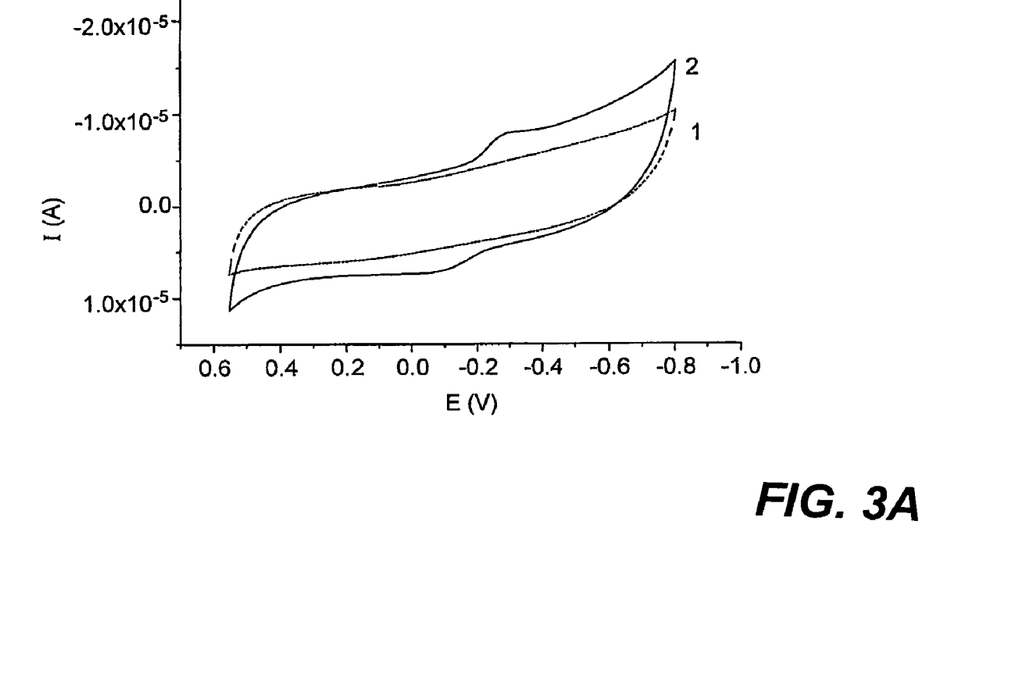
FIGS. 3A and 3B are similar to FIG. 1 and show the effect of adsorption of ubiquinone Q10 adsorbed to a GC-electrode (GCE).
Figure 3B:
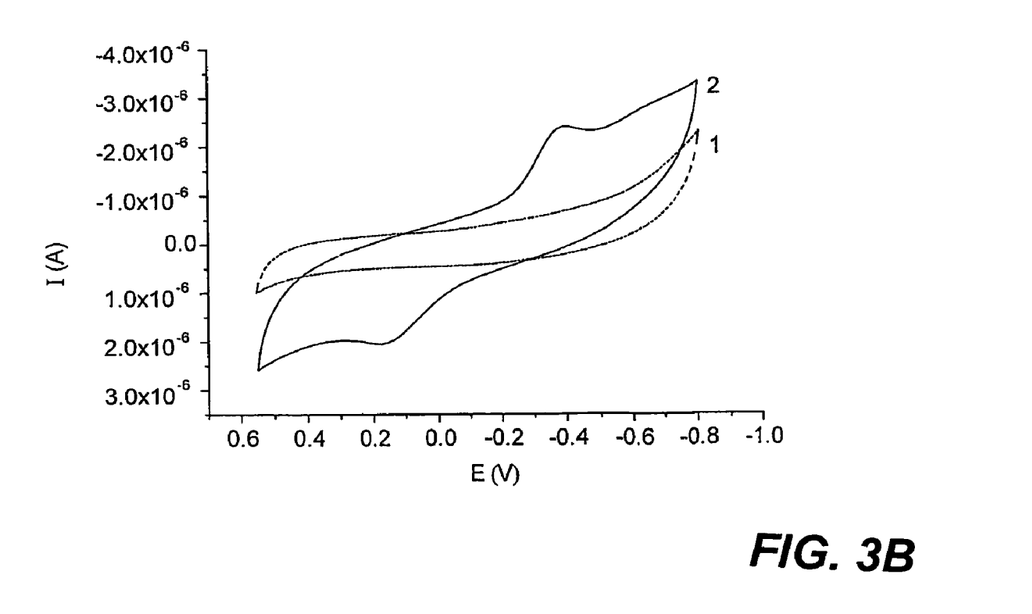

The voltammetric curve obtained with ubiquinone Q10 adsorbed on the HYDPt-1-modified GE (2 in FIG. 3A) and GCE (2 in FIG. 3B) is shown. In FIG. 3, the numeral "1" denotes an electrode covered with hydrophobin only. The shape of the curve and the linear dependence of the peak currents on the scan rate points to surface immobilization of ubiquinone. The GCE substrate covered with HYDPt-1 was found to bind Q10 in a very stable way, giving rise to ubiquinone reduction and oxidation signals which remained unchanged for several weeks.

Electroreduction of diazobenzene immobilized on electrodes modified with HYDPt-1. Diazobenzene is a small molecule with a photo- and electroactive azo group which does not undergo adsorption on a bare glassy carbon electrode. However, when adsorbed on a HYDPt-1-modified electrode, diazobenzene remains stably attached to the surface even after repeated transfers of the electrode into solutions of different pH and not containing the azocompound. Self-assembly of diazobenzene was carried out from a 1 mM methanol solution. Reduction of diazobenzene can be described as shown in Scheme 2:

Scheme 2

Figure 4:
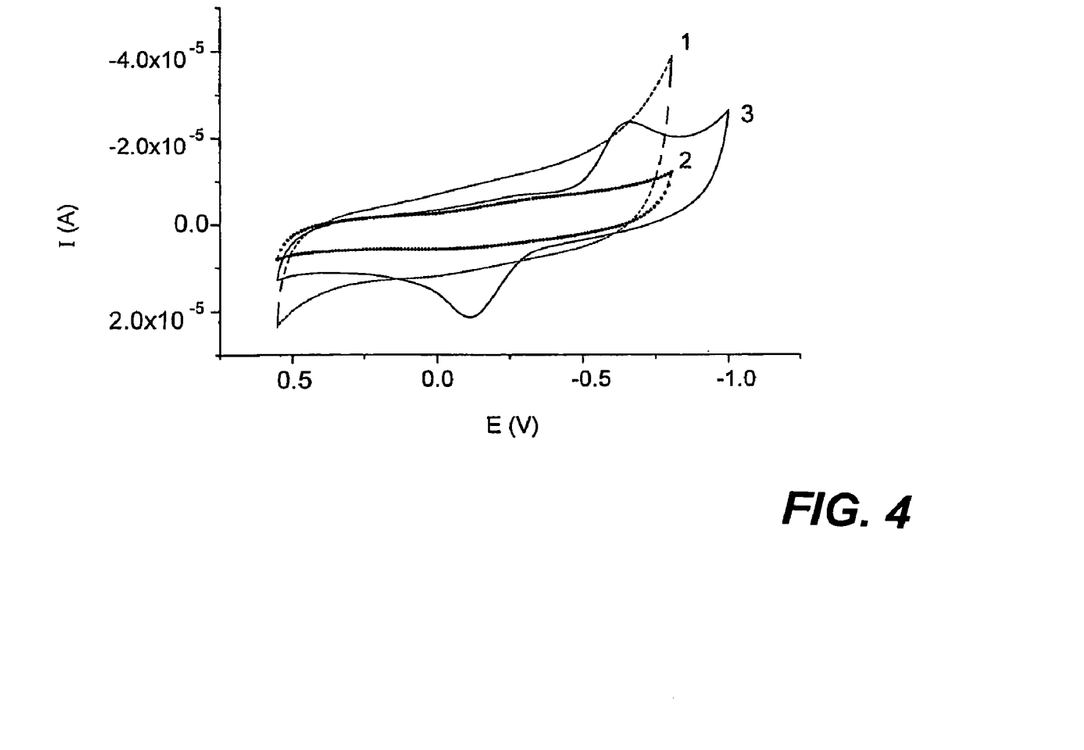
FIG. 4 shows the effect of diazobenzene on a cyclic voltammogram for a GCE.
Figure 5:
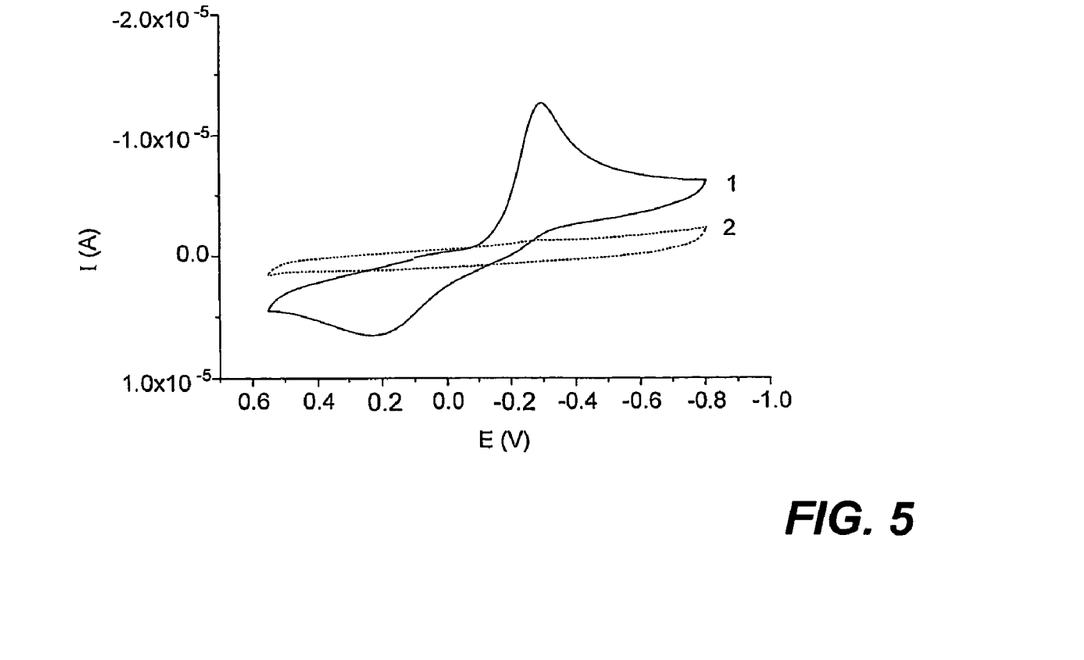
FIG. 5 is similar to FIG. 4, except that the effect of ubiquinone Q0 is shown.

FIG. 4 shows the cyclic voltammogram of diazobenzene adsorbed for 20 minutes on the HYDPt-1-modified electrode, recorded in 0.1 M Tris/HClO$_4$ solution of pH 7.0. Curve 1 was recorded after adsorption of the diazobenzene for the same lapse of time, but on the bare GCE. Curve 2 represents the electrode covered with hydrophobin, and curve 3 represents the electrode with hydrophobin and diazobenzene. The well developed reduction and oxidation peaks do not change upon repeated cycling. The peak currents increase linearly with square root of the scan rate indicating diffusion control, rather than surface-immobilized species. Since the working solution does not contain diazobenzene, this dependence can be understood in terms of diffusion of diazobenzene within the HYDPt-1 layer. Such behavior argues that in the self-assembly process, the small and hydrophobic diazobenzene molecule penetrates into, and is immobilized in, the HYDPt-1 layer. The diazobenzene incorporated into the film is being studied in our laboratories as a molecular switching device based on the cis-trans isomerization taking place on UV irradiation. Similar scan rate dependencies were observed for the Q0 molecule which has the same headgroup as Q10, but does not possess an alkyl chain (FIG. 5) and, therefore, can easily penetrate the HYDPt-1 layer. Curve 1 is a bare electrode in the presence of Q0, and curve 2 an electrode covered with hydrophobin and after adsorption of Q0.

Immobilization of glucose oxidase on a glassy carbon electrode. A glassy carbon electrode was coated with hydrophobin by placing the electrode in a solution of hydrophobin (100 µg/ml) and incubating for 15 minutes, after which the electrode was thoroughly rinsed with water. The coated electrode was submerged in a glucose oxidase-containing solution (SIGMA; 210,000 units/g of solid, final concentration 1.8 mg/ml) for two hours and rinsed with water. The electrode, after modification and functionalization with the enzyme, was used in a three electrode system including an Ag/AgCl reference electrode and a Pt counter electrode. Phosphate buffer pH 7 (25 mM) was used as electrolyte. When glucose was added, the immobilized glucose oxidase catalyzed the reaction leading to formation of hydrogen peroxide which could be detected as a small current that was proportional to the glucose concentration. The glucose oxidase remained active upon immobilization on the hydrophobin layer.

The modified electrode was stored in a sealed container, not in liquid, at 4° C., and frequently tested for activity and response to glucose. Over the period tested, 67 days, the electrode maintained its activity and was not influenced by the frequent testing.

Immobilization of cholesterol oxidase on a glassy carbon electrode. A glassy carbon electrode was coated with hydrophobin by placing the electrode in a solution of hydrophobin (100 µg/ml) and incubating for 15 minutes, after which the electrode was thoroughly rinsed with water. The coated electrode was submerged in a cholesterol oxidase-containing solution (0.5 U/ml) for two hours and rinsed with water.

The electrode, modified and functionalized with the enzyme, was placed in a three-electrode system including an Ag/AgCl reference electrode and a Pt counter electrode using phosphate buffer pH 7 (25 mM) as electrolyte. To overcome the poor solubility of cholesterol in water, the cholesterol was solubilized in isopropanol with Triton in phosphate buffer (Ropers, M-H. et al., 2001, Phys. Chem. Chem. Phys. 3:240-245). Upon addition of cholesterol, the immobilized cholesterol oxidase catalyzed the reaction and led to formation of hydrogen peroxide. The peroxide produced a small detectable current over the electrode which correlated to the concentration of cholesterol added. This example demonstrated the immobilization of cholesterol oxidase while remaining active.

Immobilization of Light Harvesting complex (LHC). Three different electrode substrates (hydrophilic GE, hydrophobic GCE or TMFE) were coated with hydrophobin (either SC3, TrSC3 or SC4) in a 100 µg/ml hydrophobin solution and placed in water. This was incubated at 25° C. for different time periods that varied from ten minutes to 16 hours. The electrodes were washed with water to remove any unbound hydrophobin; these coatings were referred to as the α-helix state.

One hydrophobin-coated and one bare electrode of each type were boiled in 2% SDS-solution for ten minutes. The SDS-treated electrodes were extensively washed with water. These coatings were referred to as the β-sheet state. The various types of coated and bare electrodes were loaded with electroactive compounds Q10, azobenzene or Q0 as described by Bilewicz et al. in J. Phys. Chem. B 2001, 105, 9772-9777, or with a mediator such as methylene blue. The various types of coated and bare electrodes either alone or not loaded with the electroactive compounds were incubated in LHC of *Cyclotella cryptica*, isolated as indicated in Rhiel et al. (Rhiel E. et al., 1997, Botanica Acta 110, 109-117), at various concentrations for two hours at 25° C. The electrodes were washed with the appropriate buffers. To assay the activity of the immobilized LHC, the electrodes (in the appropriate buffer) were placed in the dark followed by placing them in daylight and measuring the current. The dark-light cycles were repeated several times on the same day, after one day, after one week and after one month to determine the stability of the immobilized LHC.

Immobilization of CYP2D6 and CYP2C19 on an electrode surface. A glassy carbon electrode was coated with hydrophobin by emerging the electrode in a solution containing hydrophobin (100 µg/ml) for 15 minutes. The electrode was thoroughly rinsed. The cytochromes CYP2D6 and CYP2C19 were separately bound on one hydrophobin-coated electrode each, by incubation, CYP2D6 or CYP2C19-containing solution for 15 minutes and extensively rinsed. The modified electrodes were placed in a medium containing NADPH and the model substrates dextromethorphan and mephenyloin. During the incubation period, the potential was measured. The potential was induced by the contact with the substrates dextromethropan and mephenyloin. The magnitude of the potential reflects the metabolism by the iso-enzymes. After the one hour incubation, the electrodes were removed, and the substrates (dextromethorphan and mephenyloin, respectively) and products (dextrorphan and 4-hydroxymephenyloin, respectively) were quantified. The ratio of both was a reflection of the activity of the cytochromes and was correlated to the measured potential.

REFERENCES

1. Tagu, D., et al. *New Phytol.* 2001, 149, 127-135.
2. Finklea, H. O. Electrochemistry of Organized Dekker: New York, 1996; Vol. 139, pp 109-235.
3. Wösten, H. A. B. et al. *EMBO J.* 1994, 13, 5848-5854.
4. Wösten, H. A. B. et al. *Colloids Surf B: Biointerfaces* 1995, 5, 189-194.
5. Amatore, C. et al. *J. Electroanal. Chem.* 1983, 147, 39-51.
6. Bilewicz, R. et al. *Langmuir* 1991, 7, 2794-2802.
7. Wösten, H. A. B. et al. *Curr. Biol.*, 1999, 9, 85-88.
8. Wessels, J. G. H. *Adv. Microb. Physiol.* 1997, 38, 1-45.

What is claimed is:

1. A method of associating a compound with a sensor surface, said method comprising:
   coating at least a part of a surface of a sensor with a hydrophobin-like substance; and
   contacting the hydrophobin-like substance with the compound to form a non-covalent bond between the hydrophobin-like substance and the compound.

2. The method according to claim 1, wherein the compound is smaller than about 15000 daltons.

3. The method according to claim 1, wherein the compound is smaller than about 2000 daltons.

4. The method according to claim 2, wherein the compound is incorporated in the hydrophobin-like substance.

5. The method according to claim 1, wherein the compound is an electroactive compound.

6. The method according to claim 1, wherein the compound is capable of being converted into an electroactive compound.

7. The method according to claim 1, wherein the compound is larger than about 15000 daltons.

8. The method according to claim 1, wherein the compound comprises a proteinaceous substance.

9. The method according to claim 7, wherein the compound comprises an enzyme.

10. The method according to claim 7, wherein the compound comprises an antibody.

11. The method according to claim 7, wherein the compound comprises a receptor.

12. The method according to claim 1, wherein the compound is at least partly hydrophobic or comprises a hydrophobic anchor.

13. The method according to claim 1, further comprising covalently binding a second compound to the hydrophobin-like substance.

14. The method according to claim 1, further comprising:
   non-covalently binding a second compound to the hydrophobin-like substance through a third compound;
   wherein the third compound comprises an intermediate compound having an affinity for the second compound.

15. A sensor, comprising:
   a surface; and
   a coating comprising a hydrophobin-like substance and a compound non-covalently bound to the hydrophobin-like substance;
   wherein the coating covers at least part of the surface.

16. The sensor of claim 15, wherein the compound is smaller than about 15000 daltons.

17. The sensor of claim 15, wherein the compound is larger than about 15000 daltons.

18. The sensor of claim 15, wherein the compound is a proteinaceous substance.

19. The sensor of claim 15, further comprising an electrode.

20. The sensor of claim 19, wherein the electrode is selected from the group consisting of a glassy-carbon electrode, a glass electrode and a Thin Mercury Film Electrode.

21. The sensor of claim 15, further comprising an electroactive compound.

22. A method for determining a voltage difference in a solution, the method comprising:
   contacting the solution with a sensor comprising:
      a surface;
      a coating comprising a hydrophobin-like substance and a compound non-covalently bound to the hydrophobin-like substance;
      wherein the coating covers at least part of the surface;
      a sensor; and
   recording a current.

* * * * *

UNITED STATES PATENT AND TRADEMARK OFFICE
CERTIFICATE OF CORRECTION

PATENT NO. : 7,393,448 B2  Page 1 of 1
APPLICATION NO. : 10/764270
DATED : July 1, 2008
INVENTOR(S) : Ewa Maria Rogalska et al.

It is certified that error appears in the above-identified patent and that said Letters Patent is hereby corrected as shown below:

On the title page:
In ITEM (30) Foreign Application Priority Data
change "Jun. 21, 2002    (EP)  .......... 01202802"
to --Jul. 23, 2001    (EP)  .......... 01202802.3--

In the specification:
COLUMN 6,    LINE 38,        change ">about 15 kD," to --> about 15 kD,--
COLUMN 8,    LINE 6,         change ">about 15 kD," to --> about 15 kD,--
COLUMN 8,    LINES 18, 19,   change ">about 25 kD," to --> about 25 kD,--

Signed and Sealed this

Fourteenth Day of July, 2009

JOHN DOLL
*Acting Director of the United States Patent and Trademark Office*

```
                           SEQUENCE LISTING

<160> NUMBER OF SEQ ID NOS: 5

<210> SEQ ID NO 1
<211> LENGTH: 131
<212> TYPE: PRT
<213> ORGANISM: Artificial Sequence
<220> FEATURE:
<223> OTHER INFORMATION: recombinantly produced polypeptide
<220> FEATURE:
<221> NAME/KEY: SIGNAL
<222> LOCATION: (1)..(28)

<400> SEQUENCE: 1

Met Leu Lys Lys Ala Met Val Ala Ala Ala Ala Ala Ser Val Ile
 1               5                  10                  15

Gly Met Ser Ala Ala Ala Ala Pro Gln Ala Leu Ala Ile Gly Asp Asp
                20                  25                  30

Asn Gly Pro Ala Val Ala Asn Gly Asn Gly Ala Glu Ser Ala Phe Gly
                35                  40                  45

Asn Ser Ala Thr Lys Gly Asp Met Ser Pro Gln Leu Ser Leu Val Glu
         50                  55                  60

Gly Thr Leu Asn Lys Pro Cys Leu Gly Val Glu Asp Val Asn Val Ala
65                  70                  75                  80

Val Ile Asn Leu Val Pro Ile Gln Asp Ile Asn Val Leu Ala Asp Asp
                85                  90                  95

Leu Asn Gln Gln Cys Ala Asp Asn Ser Thr Gln Ala Lys Arg Asp Gly
                100                 105                 110

Ala Leu Ser His Val Leu Glu Asp Leu Ser Val Leu Ser Ala Asn Gly
            115                 120                 125

Glu Gly Arg
        130

<210> SEQ ID NO 2
<211> LENGTH: 133
<212> TYPE: PRT
<213> ORGANISM: Streptomyces coelicolor
<220> FEATURE:
<221> NAME/KEY: SIGNAL
<222> LOCATION: (1)..(28)

<400> SEQUENCE: 2

Met Ile Lys Lys Val Val Ala Tyr Ala Ala Ile Ala Ala Ser Val Met
 1               5                  10                  15

Gly Ala Ser Ala Ala Ala Ala Pro Gln Ala Met Ala Ile Gly Asp Asp
                20                  25                  30

Ser Gly Pro Val Ser Ala Asn Gly Asn Gly Ala Ser Gln Tyr Phe Gly
            35                  40                  45

Asn Ser Met Thr Thr Gly Asn Met Ser Pro Gln Met Ala Leu Ile Gln
        50                  55                  60
```

```
Gly Ser Phe Asn Lys Pro Cys Ile Ala Val Ser Asp Ile Pro Val Ser
 65                  70                  75                  80

Val Ile Gly Leu Val Pro Ile Gln Asp Leu Asn Val Leu Gly Asp Asp
                 85                  90                  95

Met Asn Gln Gln Cys Ala Glu Asn Ser Thr Gln Ala Lys Arg Asp Gly
            100                 105                 110

Ala Leu Ala His Leu Leu Glu Asp Val Ser Ile Leu Ser Ser Asn Gly
        115                 120                 125

Glu Gly Gly Lys Gly
    130

<210> SEQ ID NO 3
<211> LENGTH: 396
<212> TYPE: DNA
<213> ORGANISM: Streptomyces coelicolor

<400> SEQUENCE: 3
gtgctcaaga aggcaatggt cgccgcggcg gctgccgctt ctgtgatcgg catgtcggct      60
gccgccgctc cccaggccct ggccatcggg gacgacaacg gccggccgt ggccaacggc     120 aacggcgccg agtcggcgtt cggcaactcg gccaccaagg gcgacatgag ccccagctg     180 tcgctggtcg agggcacgct gaacaagccg tgcctcggtg tcgaggacgt caacgtcgcc     240
gtcatcaacc tcgtgccgat ccaggacatc aacgtcctgg cggacgacct gaaccagcag     300
tgcgcggaca actccacgca ggccaagcgg gacggcgccc tgtcgcacgt cctggaggac     360
ctgtcggtgc tgtcggcgaa cggcgagggc cgctga                              396

<210> SEQ ID NO 4
<211> LENGTH: 402
<212> TYPE: DNA
<213> ORGANISM: Streptomyces coelicolor

<400> SEQUENCE: 4
gtgatcaaga aggtagttgc ctacgcggcg atcgccgcct ccgtcatggg tgcctccgct      60
gccgcggccc cgcaggcgat ggcgatcggc gacgacagcg ggcccgtctc cgccaacggg     120
aacggcgcct cgcagtactt cggcaactcg atgaccacgg gcaacatgag cccgcagatg     180
gcgctcatcc agggctcgtt caacaagccg tgcatcgcgg tcagcgacat cccggtcagt     240
gtcatcggtc tggtgccgat ccaggacctc aacgtcctgg cggacgacat gaaccagcag     300
tgcgccgaga actcgacgca ggccaagcgc gacggtgcgc tggcccacct cctggaggac     360
gtctcgatcc tgtcctccaa cggcgagggc ggcaagggct ga                       402

<210> SEQ ID NO 5
<211> LENGTH: 15
<212> TYPE: PRT
<213> ORGANISM: Artificial sequence
<220> FEATURE:
<223> OTHER INFORMATION: a sequence representing a conserved sequence
      found in hydrophobins
<220> FEATURE:
<221> NAME/KEY: VARIANT
<222> LOCATION: (1)..(1)
<223> OTHER INFORMATION: Xaa can be any amino acid
<220> FEATURE:
<221> NAME/KEY: VARIANT
<222> LOCATION: (3)..(3)
<223> OTHER INFORMATION: Xaa can be any amino acid
<220> FEATURE:
<221> NAME/KEY: VARIANT
<222> LOCATION: (6)..(6)
```

```
-continued

<223> OTHER INFORMATION: Xaa can be any amino acid
<220> FEATURE:
<221> NAME/KEY: VARIANT
<222> LOCATION: (8)..(8)
<223> OTHER INFORMATION: Xaa can be any amino acid
<220> FEATURE:
<221> NAME/KEY: VARIANT
<222> LOCATION: (10)..(10)
<223> OTHER INFORMATION: Xaa can be any amino acid
<220> FEATURE:
<221> NAME/KEY: VARIANT
<222> LOCATION: (13)..(13)
<223> OTHER INFORMATION: Xaa can be any amino acid
<220> FEATURE:
<221> NAME/KEY: VARIANT
<222> LOCATION: (15)..(15)
<223> OTHER INFORMATION: Xaa can be any amino acid

<400> SEQUENCE: 5

Xaa Cys Xaa Cys Cys Xaa Cys Xaa Cys Xaa Cys Cys Xaa Cys Xaa
 1               5                  10                  15
```